United States Patent
Cohen et al.

(10) Patent No.: US 7,734,355 B2
(45) Date of Patent: Jun. 8, 2010

(54) TREATMENT OF DISORDERS BY UNIDIRECTIONAL NERVE STIMULATION

(75) Inventors: Ehud Cohen, Ganei Tikva (IL); Yossi Gross, Moshav Mazor (IL); Shai Ayal, Jerusalem (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 894 days.

(21) Appl. No.: 10/488,334

(22) PCT Filed: Jan. 23, 2002

(86) PCT No.: PCT/IL02/00068

§ 371 (c)(1),
(2), (4) Date: Jul. 6, 2004

(87) PCT Pub. No.: WO03/018113

PCT Pub. Date: Mar. 6, 2003

(65) Prior Publication Data

US 2004/0243182 A1  Dec. 2, 2004

Related U.S. Application Data

(63) Continuation-in-part of application No. 09/944,913, filed on Aug. 31, 2001, now Pat. No. 6,684,105.

(51) Int. Cl.
*A61N 1/18* (2006.01)
(52) U.S. Cl. .................... 607/118; 607/39; 607/40; 607/42; 607/44; 607/45; 607/48
(58) Field of Classification Search .............. 607/9, 607/39, 42, 44–49, 2, 40, 118
See application file for complete search history.

(56) References Cited

U.S. PATENT DOCUMENTS 3,411,507 A   11/1968   Wingrove
4,019,518 A   4/1977    Maurer et al.

(Continued)

FOREIGN PATENT DOCUMENTS

EP   0 688 577 A1   12/1995

(Continued)

OTHER PUBLICATIONS

Jone et al "Heart rate responses to selective stimulation of cardiac vagal fibres in anaesthetized cats, rats and rabbits" Journal of Physiology 1995;489; 203-214.*

(Continued)

*Primary Examiner*—Mark W Bockelman
(74) *Attorney, Agent, or Firm*—John P. White; Cooper & Dunham LLP (57) ABSTRACT

Apparatus (18) for treating a condition of a subject is provided. An electrode device (100) is adapted to be coupled to longitudinal nervous tissue (40) of the subject, and a control unit (50) is adapted to drive the electrode device to apply to the nervous tissue a current which is capable of inducing action potentials that propagate in the nervous tissue in a first direction, so as to treat the condition. The control unit is further adapted to suppress action potentials from propagating in the nervous tissue in a second direction opposite to the first direction.

18 Claims, 2 Drawing Sheets

U.S. PATENT DOCUMENTS

| | | |
|---|---|---|
| 4,161,952 A | 7/1979 | Kinney et al. |
| 4,338,945 A | 7/1982 | Kosugi et al. |
| 4,392,496 A | 7/1983 | Stanton |
| 4,535,785 A | 8/1985 | van den Honert |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples |
| 4,608,985 A | 9/1986 | Crish |
| 4,628,942 A | 12/1986 | Sweeney |
| 4,632,116 A | 12/1986 | Rosen |
| 4,649,936 A | 3/1987 | Ungar |
| 4,663,102 A | 5/1987 | Brenman et al. |
| 4,702,254 A | 10/1987 | Zabara |
| 4,739,764 A | 4/1988 | Lue |
| 4,867,164 A | 9/1989 | Zabara |
| 4,926,865 A | 5/1990 | Oman |
| 4,962,751 A | 10/1990 | Krauter |
| 5,025,807 A | 6/1991 | Zabara |
| 5,042,497 A | 8/1991 | Shapland |
| 5,069,680 A | 12/1991 | Grandjean |
| 5,170,802 A | 12/1992 | Mehra |
| 5,178,161 A | 1/1993 | Kovacs |
| 5,188,104 A | 2/1993 | Wernicke |
| 5,199,428 A | 4/1993 | Obel et al. |
| 5,199,430 A | 4/1993 | Fang |
| 5,203,326 A | 4/1993 | Collins |
| 5,205,285 A | 4/1993 | Baker, Jr. |
| 5,215,086 A | 6/1993 | Terry, Jr. |
| 5,224,491 A | 7/1993 | Mehra |
| 5,263,480 A | 11/1993 | Wernicke |
| 5,282,468 A | 2/1994 | Klepinski |
| 5,292,344 A | 3/1994 | Douglas |
| 5,299,569 A | 4/1994 | Wernicke |
| 5,314,495 A | 5/1994 | Kovacs |
| 5,330,507 A | 7/1994 | Schwartz |
| 5,335,657 A | 8/1994 | Terry, Jr. |
| 5,411,531 A | 5/1995 | Hill et al. |
| 5,423,872 A | 6/1995 | Cigaina |
| 5,437,285 A | 8/1995 | Verrier et al. |
| 5,439,938 A | 8/1995 | Snyder et al. |
| 5,454,840 A | 10/1995 | Krakovsky et al. |
| 5,507,784 A | 4/1996 | Hill et al. |
| 5,540,730 A | 7/1996 | Terry, Jr. |
| 5,540,734 A | 7/1996 | Zabara |
| 5,562,718 A | 10/1996 | Palermo |
| 5,571,150 A | 11/1996 | Wernicke |
| 5,578,061 A | 11/1996 | Stroetmann et al. |
| 5,634,462 A | 6/1997 | Tyler |
| 5,645,570 A | 7/1997 | Corbucci et al. |
| 5,690,681 A | 11/1997 | Geddes et al. |
| 5,690,691 A | 11/1997 | Chen |
| 5,700,282 A | 12/1997 | Zabara |
| 5,707,400 A | 1/1998 | Terry, Jr. |
| 5,711,316 A | 1/1998 | Elsberry et al. |
| 5,716,385 A | 2/1998 | Mittal |
| 5,755,750 A | 5/1998 | Petruska |
| 5,824,027 A | 10/1998 | Hoffer |
| 5,832,932 A | 11/1998 | Elsberry et al. |
| 5,833,709 A | 11/1998 | Rise et al. |
| 5,836,994 A | 11/1998 | Bourgeois |
| 5,916,239 A | 6/1999 | Geddes et al. |
| 5,938,584 A | 8/1999 | Ardito et al. |
| 6,026,326 A | 2/2000 | Bardy |
| 6,058,331 A | 5/2000 | King et al. |
| 6,061,596 A | 5/2000 | Richmond et al. |
| 6,066,163 A | 5/2000 | John |
| 6,073,048 A | 6/2000 | Kieval et al. |
| 6,083,249 A | 7/2000 | Familoni |
| 6,086,525 A | 7/2000 | Davey et al. |
| 6,091,922 A | 7/2000 | Bisaiji |
| 6,091,977 A | 7/2000 | Tarjan et al. |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| 6,146,335 A | 11/2000 | Gozani |
| 6,161,029 A | 12/2000 | Spreigl et al. |
| 6,167,304 A | 12/2000 | Loos |
| 6,169,924 B1 | 1/2001 | Meloy et al. |
| 6,205,359 B1 | 3/2001 | Boveja |
| 6,230,061 B1 | 5/2001 | Hartung |
| 6,240,314 B1 | 5/2001 | Plicchi et al. |
| 6,266,564 B1 | 7/2001 | Hill et al. |
| 6,272,377 B1 | 8/2001 | Sweeney et al. |
| 6,341,236 B1 | 1/2002 | Osorio et al. |
| 6,356,784 B1 | 3/2002 | Lozano et al. |
| 6,366,813 B1 | 4/2002 | DiLorenzo |
| 6,381,499 B1 | 4/2002 | Taylor et al. |
| 6,400,982 B2 | 6/2002 | Sweeney et al. |
| 6,405,079 B1 | 6/2002 | Ansarinia |
| 6,449,507 B1 | 9/2002 | Hill et al. |
| 6,463,328 B1 | 10/2002 | John |
| 6,473,644 B1 | 10/2002 | Terry, Jr. et al. |
| 6,493,585 B2 | 12/2002 | Plicchi et al. |
| 6,542,774 B2 | 4/2003 | Hill et al. |
| 6,564,096 B2 | 5/2003 | Mest |
| 6,587,727 B2 | 7/2003 | Osorio et al. |
| 6,600,956 B2 | 7/2003 | Maschino et al. |
| 6,610,713 B2 | 8/2003 | Tracey |
| 6,622,041 B2 | 9/2003 | Terry et al. |
| 6,628,987 B1 | 9/2003 | Hill et al. |
| 6,658,297 B2 | 12/2003 | Loeb |
| 6,668,191 B1 | 12/2003 | Boveja |
| 6,671,556 B2 | 12/2003 | Osorio et al. |
| 6,735,474 B1 | 5/2004 | Loeb et al. |
| RE38,705 E | 2/2005 | Hill et al. |
| 6,865,416 B2 | 3/2005 | Dev et al. |
| 6,885,888 B2 * | 4/2005 | Rezai ............................ 607/9 |
| 6,895,280 B2 | 5/2005 | Meadows et al. |
| 6,928,320 B2 | 8/2005 | King |
| 6,934,583 B2 | 8/2005 | Weinberg et al. |
| 6,985,774 B2 | 1/2006 | Kieval et al. |
| 7,050,846 B2 | 5/2006 | Sweeney et al. |
| 7,076,299 B2 | 7/2006 | Thong |
| 7,076,307 B2 | 7/2006 | Boveja et al. |
| 2001/0003799 A1 | 6/2001 | Boveja |
| 2002/0035335 A1 | 3/2002 | Schauerte |
| 2002/0055761 A1 | 5/2002 | Mann et al. |
| 2002/0107553 A1 | 8/2002 | Hill et al. |
| 2003/0018365 A1 | 1/2003 | Loeb |
| 2003/0195574 A1 | 10/2003 | Osorio et al. |
| 2003/0216775 A1 | 11/2003 | Hill et al. |
| 2003/0229380 A1 | 12/2003 | Adams et al. |
| 2003/0233129 A1 | 12/2003 | Matos |
| 2003/0236557 A1 | 12/2003 | Whitehurst et al. |
| 2003/0236558 A1 | 12/2003 | Whitehurst et al. |
| 2004/0015204 A1 | 1/2004 | Whitehurst et al. |
| 2004/0015205 A1 | 1/2004 | Whitehurst et al. |
| 2004/0048795 A1 | 3/2004 | Ivanova et al. |
| 2004/0059392 A1 | 3/2004 | Parramon et al. |
| 2004/0138721 A1 | 7/2004 | Osorio et al. |
| 2004/0152958 A1 | 8/2004 | Frei et al. |
| 2004/0158119 A1 | 8/2004 | Osorio et al. |
| 2004/0215289 A1 | 10/2004 | Fukui |
| 2004/0249416 A1 | 12/2004 | Yun et al. |
| 2005/0131467 A1 | 6/2005 | Boveja |
| 2005/0187584 A1 | 8/2005 | Denker et al. |
| 2005/0222644 A1 | 10/2005 | Killian et al. |
| 2006/0015153 A1 | 1/2006 | Gliner et al. |
| 2006/0052831 A1 | 3/2006 | Fukui |

| | | |
|---|---|---|
| 2006/0074450 A1 | 4/2006 | Boveja et al. |
| 2006/0129205 A1 | 6/2006 | Boveja et al. |

FOREIGN PATENT DOCUMENTS

| | | |
|---|---|---|
| EP | 0831954 | 4/1998 |
| WO | WO-01/10375 A2 | 2/2001 |
| WO | WO-01/10432 | 2/2001 |
| WO | WO-01/26729 | 4/2001 |

OTHER PUBLICATIONS

U.S. Appl. No. 60/263,834, entitled "Selective Blocking of Nerve Fibers", filed Jan. 25, 2001.

Ungar, I. J., et al. "Generation of Unidirectionally Propagating Action Potentials Using a Monopolar Electrode Cuff", Annals of Biomedical Engineering, vol. 14, pp. 437-450, 1986.

Sweeney, James D., et al. "An Asymmetric Two Electrode Cuff for Generation of Unidirectionally Propagated Action Potentials", IEEE Transactions on Biomedical Engineering, vol. BME-33, No. 6, Jun. 1986.

Naples, Gregory G., et al. "A Spiral Nerve Cuff Electrode for Peripheral Nerve Stimulation", IEEE Transactions of Biomedical Engineering, vol. 35, No. 11, Nov. 1998, pp. 905-916.

Sweeney, James D., et al. "A Nerve Cuff Technique for Selective Excitation of Peripheral Nerve Trunk Regions", IEEE Transactions on Biomedical Engineering, vol. 37, No. 7, Jul. 1990.

Van Den Honert, et al. "Generation of Unidirectionally Propagated Action Potentials in a Peripheral Nerve by Brief Stimuli", Science magazine, vol. 206, Dec. 14, 1979, pp. 1311-1312.

Van Den Honert, et al. "A Technique for Collision Block of Peripheral Nerve: Frequency Dependence", IEEE Transactions of Biomedical Engineering, vol. BME-28, No. 5, May 1981, pp. 379-382.

Rijkhoff, N.J.M., et al. "Orderly recruitment of motoneurons in an acute rabbit model", 20th Annual International Conference of the IEEE Engineering in Medicine and Biology Society, vol. 20, No. 5, 1998, pp. 2564-2565.

Baratta, et al. "Orderly stimulation of Skeletal Muscle Motor Units with Tripolar Nerve Cuff Electrode", IEEE Transactions of Biomedical Engineering, vol. 36, No. 8, Aug. 1989, pp. 836-843.

Devor, M. "Pain Networks", Handbook of Brand Theory and Neural Networks, Ed. M.A. Arbib, MIT Press, p. 698, 1998.

U.S. Appl. No. 09/824,682 entitled "Method and Apparatus for Selective Control of Nerve Fibers", filed Apr. 4, 2001.

Cortese, J.F. "Vagus Nerve Stimulation for Control of Intractable Epileptic Seizures" available at http://www.science.wayne.edu/~bio340/StudentPages/corese/. May 31, 2001.

Website: http://www.bcm.tmc.edu/neurol/struct/epilep/epilipsy_vagus.html, May 31, 2001.

Fitzpatrick, et al. "A Nerve Cuff Design for the Selective Activation and Blocking of Myelinated Nerve Fibres", Annual Conference of the IEEE Engineering in Medicine and Biology Society, vol. 13, No. 2, 1991.

Zhang, Y., et al. "Optimal Ventricular Rate Slowing During Atrial Fibrillation by Feedback AV Nodal-Selective Vagal Stimulation", Am. J. Physiol. Heart Circ. Physiol. 282:H1102-H1110, 2002.

Rijkhoff, N.J.M., et al., "Selective Stimulation of Small Diameter Nerve Fibers in a Mixed Bundle", Proceedings of the Annual Project Meeting Sensations/Neuros and Mid Term Review Meeting Neuros, pp. 21-23, Apr. 1999.

Manfredi, M., "Differentiating Blocks of conduction of larger fibers in peripheral nerve by direct current", Arch. Ital. Biol., vol. 108, pp. 52-71, 1970.

Don W. Wallick, et al., "Selective AV nodal vagal stimulation improves hemodynamics during acute atrial fibrillation in dogs", Am J. Physiol Heart Circ Physiol, 281: H1490-H1497, 2001.

Masato Tsuboi et al., "Inotropic, chronotropic and dromotropic effects mediated via parasympathetic ganglia in the dog heart", Am J. Physiol Heart Circ Physiol, 279: H1201-H1207, 2000.

C.W. Chiou et al., "Efferent vagal innervation of the canine atria and sinus and atrioventricular nodes", Circulation, 1997; 95:2573.

P. Schauerte, et al, "Catheter stimulation of cariac parasympathetic nerves in humans", available at http://www.circulationaha.org, pp. 2430-2435, 2001.

M. Hirose, "Pituitary adenylate cyclase-activating polypeptide-27 causes a biphasic chronotropic effect and atrial fibrillation in autonomically decentralized, anesthetized dogs", The Journal of Pharmacology and Experimental Therapeutics, vol. 283, No. 2, pp. 478-487, 1997.

Furukawa Y et al., "Differential blocking effects of atropine and gallamine on negative chrontropic and dromotropic responses to vagus stimulation in anesthetized dogs," J Pharmacol Exp. Ther. 251(3):797-802 (1989).

Bluemel KM, "Parasympathetic postganglionic pathways to the sinoatrial node, " J Physiol. 259 (5 Pt 2): H1504-10 (1990).

Mazgalev TN, "AV Nodal Physiology," Heart Rhythm Society (www.hrsonline.org), no date.

Bibevski S et al. "Ganglionic Mechanisms Contribute to Diminished Vagal Control in Heart Failure," Circulation 99:2958-2963(1999).

Garrigue S et al., "Post-ganglionic vagal stimulation of the atrioventricular node reduces ventricular rate during atrial fibrillation, "Pace 21(4), Part II, 878 (1998).

Chen SA et al., "Intracardiac stimulation of human parasympathetic nerve fibers induces negative dromotropic effects: implication with the lesions of radiofrequency catheter ablation," J Cardiovasc Electrophysiol. 9(3):245-52 (1998).

Cooper et al., "Neural effects on sinus rate and atrial ventricular conduction produced by electrical stimulation from a transvenous electrode catheter in the canine right pulmonary artery" Circ Res vol. 46(1):48-57 (1980).

Waninger MS et al., "Electrophysiological control of ventricular rate during atrial fibrillation," Pace 23:1239-1244 (2000).

Goldberger JJ et al., "New technique for vagal nerve stimulation," J Neurosci Methods. 91(1-2):1089-14 (1999).

Carlson MD et al., "Selective stimulation of parasympathetic nerve fibers to the human sinoatrial node," Circulation 85:1311-1317 (1992).

Pagè PL et al., "Regional distribution of atrial electrical changes induced by stimulation of extracardiac and intracardia neural elements," J. Thorac Cardiovasc Surg. 109(2):377-388 (1995).

Zi-Ping Fang, et al., (1991) "Selective Activation of Small Motor Axons by Quasitrapezodial Current Pulses", IEEE Transactions on Biomedical Engineering 38(2): 168-171.

Office Action dated Jun. 27, 2008 which was issued during the prosecution of Applicant's U.S. Appl. No. 10/205,475.

Office Action issued Aug. 6, 2009, in connection with U.S. Appl. No. 10/205,475, filed Jul. 24, 2002.

European Office Action, issued Apr. 3, 2009, in connection with European Patent Application No. 02716294.0, filed Jan. 23, 2002.

* cited by examiner

TREATMENT OF DISORDERS BY UNIDIRECTIONAL NERVE STIMULATION

CROSS-REFERENCES TO RELATED APPLICATIONS

This application is a continuation-in-part of U.S. patent application Ser. No. 09/944,913, filed Aug. 31, 2001, entitled, "Treatment of disorders by unidirectional nerve stimulation." which is assigned to the assignee of the present patent application and is incorporated herein by reference.

FIELD OF THE INVENTION

The present invention relates generally to treating patients by application of electrical signals to a selected nerve or nerve bundle, and specifically to methods and apparatus for stimulating nerve tissue while minimizing possible accompanying side effects.

BACKGROUND OF THE INVENTION

The use of nerve stimulation for treating and controlling a variety of medical, psychiatric, and neurological disorders has seen significant growth over the last several decades. In particular, stimulation of the vagus nerve (the tenth cranial nerve) has been the subject of considerable research. The vagus nerve is composed of somatic and visceral afferents (inward conducting nerve fibers, which convey impulses toward the brain) and efferents (outward conducting nerve fibers, which convey impulses to an effector to regulate activity such as muscle contraction or glandular secretion). The vagus nerve is responsible for controlling and/or receiving feedback from various glands, the pharynx, larynx, heart, lungs, liver, stomach, intestine, and ureters. Because of its large number of functions with respect to a range of body systems, the vagus nerve is preferred in many applications for purposes of modulating the functions of designated organs or portions of the central nervous system (CNS).

U.S. Pat. No. 5,540,730 to Terry et al., which is incorporated herein by reference, describes a method for treating motility disorders by applying a signal to the vagus nerve of a patient, in order to stimulate or inhibit neural impulses and produce excitatory or inhibitory neurotransmitter release by the nerve, according to the specific nature of the motility disorder.

U.S. Pat. Nos. 5,188,104 and 5,263,480 to Wernicke et al., which are incorporated herein by reference, describe a method for treating compulsive eating disorders by applying a stimulating signal to the vagus nerve of the patient appropriate to alleviate the effect of the eating disorder. For example, in cases where the disorder is compulsive eating, the stimulating signal is described as being calibrated to produce a sensation of satiety in the patient. In cases where the disorder is compulsive refusal to eat (anorexia nervosa), the stimulating signal is described as being calibrated to produce a sensation of hunger or to suppress satiety in the patient.

U.S. Pat. No. 5,571,150 to Wernicke et al., which is incorporated herein by reference, describes a method for treating a comatose patient by stimulating a cranial nerve, preferably the vagus nerve, in order to modulate the activity of the nerve in an effort to rouse the patient from the coma.

U.S. Pat. Nos. 4,702,254, 4,867,164 and 5,025,807 to Zabara, which are incorporated herein by reference, generally describe methods for controlling or preventing epileptic seizures and other motor disorders by stimulating the vagus nerve.

U.S. Pat. No. 6,205,359 to Boveja, which is incorporated herein by reference, describes apparatus for treating various forms of epilepsy and involuntary movement disorders by electrical stimulation of the left vagus nerve.

U.S. Pat. No. 5,205,285 to Baker, which is incorporated herein by reference, describes a device designed to avoid undesirable voice modulation of patients undergoing vagal stimulation therapy, while maintaining a bias in certain circumstances toward ongoing delivery of the therapy. In essence, this device requires the addition of sensing means to detect the patient's attempts at speech, responsive to which the device halts or delays the vagal stimulation during the time that speech attempts continue to be detected.

U.S. Pat. No. 5,299,569 to Wernicke et al., which is incorporated herein by reference, describes a method for treating and controlling neuropsychiatric disorders, including schizophrenia, depression and borderline personality disorder, by selectively applying a predetermined electrical signal to the patient's vagus nerve, in order to alleviate the symptoms of the disorder being treated.

U.S. Pat. No. 5,335,657 to Terry et al., which is incorporated herein by reference, describes a method for treating and controlling sleep disorders by applying an electrical signal to the vagus nerve in order to modulate electrical activity of afferent fibers of the nerve.

U.S. Pat. No. 5,707,400 to Terry et al., which is incorporated herein by reference, describes a method for treating patients suffering from refractory hypertension, also by stimulating the vagus nerve.

As is seen from this list of patents, stimulation of the nervous system, particularly the vagus nerve, for therapeutic purposes has been the subject of a considerable amount of research and application to medical, psychiatric, and neurological disorders. However, other than the problem of speech impairment addressed by the above-cited U.S. Pat. No. 5,205,285 to Baker, the possible unwanted side effects, both proven and potential, of selective stimulation of the vagus nerve, have not been given extensive consideration.

U.S. Pat. No. 5,282,468 to Klepinski, which is incorporated herein by reference, describes an implantable neural electrode.

U.S. Pat. No. 4,628,942 to Sweeney et al., which is incorporated herein by reference, describes an asymmetric, shielded, two-electrode cuff for stimulating a nerve.

U.S. Pat. No. 4,535,785 to van den Honert et al., describes implantable electronic apparatus.

U.S. Pat. No. 4,602,624 to Naples et al., which is incorporated herein by reference, describes an implantable electrode cuff for applying signals to nerves.

U.S. Pat. No. 5,199,430 to Fang et al., which is incorporated herein by reference, describes implantable electronic apparatus for assisting the urinary sphincter to relax.

U.S. Pat. No. 5,215,086 to Terry et al., which is incorporated herein by reference, describes a method for applying electrical stimulation to treat migraine headaches.

U.S. Pat. No. 5,755,750 to Petruska et al., which is incorporated herein by reference, describes a method for selectively inhibiting activity in nerve fibers.

U.S. Pat. Nos. 4,649,936 to Ungar et al., and 4,608,985 to Chrish et al., which are incorporated herein by reference, describe apparatus and methods for selectively blocking action potentials passing along a nerve trunk.

PCT Patent Publication WO 01/10375 A2 to Felsen et al., which is incorporated herein by reference, describes a method for inhibiting action potential generation in nervous tissue.

The following articles may be of interest, and are incorporated herein by reference:

"Generation of unidirectionally propagating action potentials using a monopolar electrode cuff," Annals of Biomedical Engineering, vol. 14, pp. 437-450, 1986 by Ira J. Ungar et al.

"An asymmetric two electrode cuff for generation of unidirectionally propagated action potentials," IEEE Transactions on Biomedical Engineering, vol. BME-33, No. 6, June 1986 by James D. Sweeney et al.

"A spiral nerve cuff electrode for peripheral nerve stimulation," by Gregory G. Naples et al., IEEE Transactions on Biomedical Engineering, vol. 35, No. 11, November 1988.

"A nerve cuff technique for selective excitation of peripheral nerve trunk regions," by James D. Sweeney et al., IEEE Transactions on Biomedical Engineering, vol. 37, No. 7, July 1990.

"Generation of unidirectionally propagated action potentials in a peripheral nerve by brief stimuli," Science, vol. 206, pp. 1311-1312, December 1979.

"Generation of unidirectionally propagated action potentials in a peripheral nerve by brief stimuli," van den Honert et al., 206 Science 1311-1312, (Dec. 14, 1979).

"A technique for collision block of peripheral nerve: Frequency dependence," van den Honert, C., Mortimer, J. T.: MP-12, IEEE Trans. Biomed. Eng. 28:379-382, 1981.

"A technique for collision block of peripheral nerve: Single stimulus analysis," van den Honert, C., Mortimer, J. T.: MP-11, IEEE Trans. Biomed. Eng. 28:373-378, 1981.

"A Nerve Cuff Design for the Selective Activation and Blocking of Myelinated Nerve Fibers," D. M. Fitzpatrick et al., Ann. Conf. of the IEEE Eng. in Medicine and Biology Soc., Vol. 13, No. 2, pp. 906, 1991.

"Acute Animal Studies on the Use of Anodal Block to Reduce Urethral Resistance in Sacral Root Stimulation," N. J. M. Rijkhof et al., IEEE Transactions on Rehabilitation Engineering, Vol. 2, No. 2, pp. 92, 1994.

"Orderly Recruitment of Motoneurons in an Acute Rabbit Model," N. J. M. Rijkhoff et al., Ann. Conf. of the IEEE Eng., Medicine and Biology Soc., Vol. 20, No. 5, pp. 2564, 1998.

"Orderly Stimulation of Skeletal Muscle Motor Units with Tripolar Nerve Cuff Electrode," R. Bratta et al., IEEE Transactions on Biomedical Engineering, Vol. 36, No. 8, pp. 836, 1989.

U.S. Pat. No. 5,423,872 to Cigaina, which is incorporated herein by reference, describes a method for pacing the stomach in order to alter its natural rhythm. The principle espoused in Cigaina is that by altering the rhythm, one can either delay or speed up gastric emptying. Cigaina indicates that many different disorders, including gastroesophageal reflux disorder (GERD), can be treated using the rhythm altering method.

U.S. Pat. No. 5,716,385 to Mittal et al., which is incorporated herein by reference, describes a system to treat GERD by stimulating the skeletal muscle tissue of the crural diaphragm whenever myoelectric measurements made on the diaphragm are indicative of relaxation thereof. Stimulation of the diaphragm is intended to indirectly cause contraction of the lower esophageal sphincter (LES), and thereby inhibit a reflux event which is assumed to accompany relaxation of the diaphragm.

U.S. Pat. No. 6,097,984 to Douglas, which is incorporated herein by reference, discloses a system to treat GERD by continually simulating the LES of a patient in order to maintain it in a closed state, thereby preventing reflux. Stimulation is removed only when swallowing is detected, to allow food pass into the stomach.

U.S. Pat. Nos. 6,104,955, 6,091,992, and 5,836,994 to Bourgeois, 6,026,326 to Bardy, 6,083,249 to Familoni, 5,690, 691 to Chen, 5,292,344 to Douglas, and 3,411,507 to Wingrove, which are incorporated herein by reference, describe methods and apparatus for electrical simulation of the GI tract to treat various physiological disorders.

U.S. Pat. Nos. 4,585,005 to Lue et al., 4,663,102 to Brenman et al., 5,439,938 to Snyder et al., 5,454,840 to Krakovsky et al., 5,938,584 to Ardito et al., and 6,169,924 to Meloy et al., which are incorporated herein by reference, describe systems for applying electrical stimulation to treat erectile dysfunction.

U.S. Pat. No. 4,338,945 to Kosugi et al., which is incorporated herein by reference, describes a randomized electrical stimulation system for providing pain relief. In particular, the Kosugi patent describes a system for generating electrical pulses for relieving a patient's pain that includes a pulse generator and a controller for modulating the parameters of the output pulses of the pulse generator to fluctuate in accordance with a 1/f rule, i.e., such that the spectral density of the fluctuation varies inversely with the frequency. It is noted in that patent that conventional stimulation pulse trains have ". . . stimulation parameters such as pulse rate, pulse width and pulse amplitude [which] do not change in time course. After a long-time use of such a stimulation which adopts uniform or simple periodic stimuli, the nervous system reveals adaptation effect against the stimuli."

SUMMARY OF THE INVENTION

It is an object of some aspects of the present invention to provide apparatus and methods for treating and controlling a medical condition by application of electrical signals to a selected nerve or nerve bundle.

It is also an object of some aspects of the present invention to provide apparatus and methods for treating and controlling a medical condition by application of electrical signals to a selected nerve or nerve bundle while minimizing adverse side effects.

It is a further object of some aspects of the present invention to provide apparatus and methods for treatment of sleep disorders while minimizing adverse side effects.

It is still a further object of some aspects of the present invention to provide apparatus and methods for treatment of neuropsychiatric disorders while minimizing adverse side effects.

It is yet a further object of some aspects of the present invention to provide apparatus and methods for treatment of eating disorders, while minimizing adverse side effects caused by stimulation of the nerves controlling the digestive system.

It is an additional object of some aspects of the present invention to provide apparatus and methods for treatment of motility disorders, while minimizing undesired side effects caused by stimulation of the nerves controlling the digestive system.

It is yet an additional object of some aspects of the present invention to provide apparatus and methods for rousing comatose patients, while minimizing adverse effects upon physiological functions.

It is still an additional object of some aspects of the present invention to provide apparatus and methods for treating epilepsy and involuntary movement disorders while minimizing unwanted side effects such as impairment of speech.

It is also an object of some aspects of the present invention to provide apparatus and methods for treating hypertension while minimizing unwanted side effects.

It is a further object of some aspects of the present invention to provide improved methods and apparatus for treating erectile dysfunction or other sexual disorders in males and females.

It is still a further object of some aspects of the present invention to provide improved methods and apparatus for treating congestive heart failure, arrhythmia, and other cardiac pathologies.

It is yet a further object of some aspects of the present invention to provide improved methods and apparatus for treating pulmonary pathologies such as chronic obstructive pulmonary disease (COPD).

It is also an object of some aspects of the present invention to provide improved methods and apparatus for treating hyperhidrosis.

In preferred embodiments of the present invention, apparatus for treating a specific condition comprises a set of one or more electrode devices that are applied to one or more selected sites of the central or peripheral nervous system of a patient. A control unit preferably drives the electrode devices to: (a) apply signals which induce the propagation of nerve impulses in a desired direction in order to treat the condition, and (b) suppress artificially-induced nerve impulses in the opposite direction in order to minimize adverse side effects of the signal application.

For some applications of the present invention, the signal is applied to a nerve such as the vagus nerve, in order to stimulate efferent fibers and increase the motor activity of the small intestine and colon, and thereby treat motility disorders. Simultaneously, action potential propagation is inhibited in afferent fibers responsive to the application of the signals. In the prior art, such as that described in the above-cited U.S. Pat. No. 5,540,730 to Terry et al., the vagus nerve is stimulated so as to influence the motor activity of the small intestine and colon. However, an unintended result of applying the method of the Terry patent is that, when the nerve is stimulated, action potentials are induced in both directions (stimulating afferent and efferent fibers). Stimulation of the vagus nerve as a whole may thus produce undesired afferent stimulation, which may in turn result in, for example, the initiation of undesired or counterproductive feedback to the brain, and resultant undesired sensations or activity of the digestive system (e.g., nausea). Advantageously, and unlike the prior art, application of these embodiments of the present invention substantially stimulates only the intended efferent fibers, and reduces or eliminates the transmission of sensory signals to the CNS that could cause such undesirable responses in the digestive system.

For some applications of the present invention, the signal is applied to a portion of the vagus nerve innervating the stomach in order to stimulate sensory fibers and thereby produce a sensation, e.g., satiety or hunger. In the prior art, such as that described in the above-cited U.S. Pat. No. 5,263,480 to Wernicke et al., the vagus nerve is stimulated so as to induce certain sensory messages to propagate to the brain. However, upon the application of stimulation as described by Wernicke, action potentials are induced in both directions—on afferent and efferent fibers—and may thus generate unwanted effector responses. Depending upon the location on the vagus nerve at which stimulation is applied, such impulses may, for example, stimulate the glands of the stomach to secrete excessive hydrochloric acid, or they may reduce or otherwise affect the heartbeat of the patient. Unlike the prior art, application of this embodiment of the present invention generates substantially only sensory signals, and generally does not cause efferent signals to be transmitted to the effectors that could result in such undesirable responses.

For some applications, the signal is applied to the vagus nerve so as to modulate electrical activity in the brain, and thereby rouse a patient from a comatose condition. At the same time, the electrode devices are driven to inhibit action potentials in efferent fibers which would generally arise as a result of the application of the signal. In the prior art, such as that described in U.S. Pat. No. 5,571,150 to Wernicke et al., the vagus nerve in the neck is stimulated so as to cause afferent nerve fibers to conduct modified electrical patterns toward the reticular formation. However, inadvertent stimulation of efferent fibers resulting from the bi-directional nature of artificial nerve stimulation may result in undesirable motor, glandular or cardiac activity. Unlike the prior art, this application of the present invention inhibits action potentials in the efferent fibers, and consequently generally does not cause unwanted efferents to be generated.

Alternatively, the signal is applied to the vagus nerve to treat epilepsy and involuntary movement disorders, while action potential propagation responsive to the signal in efferent fibers is suppressed. In the prior art, either the left or right vagus nerve is stimulated as described in the above-cited Zabara and Boveja patents. The basic premise of vagal nerve stimulation for control of epileptic seizures is that vagal afferents have a diffuse central nervous system (CNS) projection, and activation of these pathways has a widespread effect on neuronal excitability. However, the mechanism by which vagal stimulation exerts its influence on seizures is not well understood.

The inventors of the present invention believe that the techniques described in the Zabara and Boveja patents induce unintended and, at least to some extent, undesirable accompanying effects resulting from the stimulation of efferent fibers at the same time as the treatment is being applied. It is well known, for example, that stimulation of the right vagus can lead to profound bradycardia (slowing of the heartbeat), which is an unwanted and unnecessary complication. Additionally, it has been determined that a side effect of vagal stimulation in epileptic patients is the presence of a noticeable modulation or reduction of the patient's voice when he or she tries to speak during application of the stimulating signals to the nerve. U.S. Pat. No. 5,205,285 to Baker, cited above, addresses the problem of voice modulation, but requires the addition of a sensor to detect the patient's speech and simply terminates the vagal stimulation, i.e., the desired treatment, whenever speech attempts continue to be detected. A drawback of this solution is that beneficial therapy may be unduly inhibited in favor of cosmetic or secondary considerations. Unlike the limitations of the prior art, however, application of this embodiment of the present invention substantially precludes the onset of these accompanying effects by permitting nerve impulses to travel only in the desired direction.

For some applications of the present invention, the signal is applied to the vagus nerve in order to treat and control sleep disorders or hypertension, while inhibiting action potential propagation in efferent fibers responsive to the applied signal. In the prior art, such as that described in U.S. Pat. Nos. 5,335,657 and 5,707,400 to Terry et al., bi-directional impulses are generated by the stimulation, resulting in both the desired treatment as well as unintended and not necessarily beneficial accompanying physiological responses. Unlike the prior art, however, application of this embodiment of the present invention substantially does not stimulate electrical activity of efferent fibers that may generate unwanted visceral, glandular, or motor responses.

In a preferred embodiment, the signal is applied to the pelvic nerve, or another nerve, in order to treat erectile dysfunction. Preferably, the signal is configured so as to cause the arterial dilation responsible for erection, and is applied in a stimulatory mode to parasympathetic fibers, and/or in an inhibitory mode to sympathetic fibers. Alternatively or additionally, in order to support ejaculation preferably following a period of erection, the signal is applied in an inhibitory mode to parasympathetic fibers, and/or in a stimulatory mode to sympathetic fibers. For some applications, the signal is applied in a unidirectional mode, so as to prevent undesired action potentials from being conveyed to the brain in response to the applied signal. For other applications, the signal is applied in a unidirectional mode, so as to prevent undesired action potentials from being conveyed to the penis in response to the applied signal.

For some embodiments in which it is desired to assist a patient in facilitating or maintaining an erection, signal application modes are utilized to block or reduce action potentials in sympathetic nerve fibers such as sympathetic C fibers that would otherwise: (a) be conveyed to the penis, (b) cause the constriction of arteries thereof, and, consequently, (c) inhibit an erection. By blocking these action potentials, the inhibition to erection is removed, and the erection can occur. Preferably, in order to facilitate erection, a series of pulses are applied to a site on the pelvic nerve or another nerve, so as to generate action potentials which travel in a central direction (i.e., towards the brain or spinal cord), and then collide with peripherally-directed, erection-inhibiting natural action potentials and terminate the propagation of these natural action potentials. Simultaneously, anodal blocking or another technique is used to prevent the applied pulses from inducing new peripherally-directed action potentials along the same fibers, which in the absence of the anodal block would inhibit an erection.

It is to be understood that whereas these embodiments of the present invention are described with respect to enhancing sexual functioning in a male, the same principles may be adapted for use in enhancing sexual functioning in a female, mutatis mutandis, e.g., so as to facilitate the engorgement of vulval erectile tissue with blood, or to relieve vaginismus. It is similarly to be understood that whereas these treatments for erectile dysfunction are described with respect to signal application to the pelvic nerve, this is by way of illustration and not limitation, and the scope of the present invention includes the application of electrical waveforms to other nerves, such as the cavernous nerve, the pudendal nerve, or to sacral nerve roots.

In summary, the stimulation of nerve impulses in one direction while suppressing impulses in the opposite direction is preferably used to obtain the benefits of various new or prior art therapeutic treatments, including, but not limited to, those described in the references cited herein, while reducing or eliminating adverse and/or unintended side effects.

There is therefore provided, in accordance with a preferred embodiment of the present invention, a method for treating a condition of a subject, including:

driving into longitudinal nervous tissue of the subject a current which is capable of inducing action potentials that propagate in the nervous tissue in a first direction, so as to treat the condition; and suppressing action potentials from propagating in the nervous tissue in a second direction opposite to the first direction.

For some applications, driving the current includes driving a current capable of inducing action potentials that propagate in the nervous tissue in an afferent direction with respect to the central nervous system of the subject. For other applications, driving the current includes driving a current capable of inducing action potentials that propagate in the nervous tissue in an efferent direction with respect to the central nervous system of the subject.

In various preferred embodiments, driving the current includes driving the current into one or more of the following: a vagus nerve of the subject, a pelvic nerve of the subject, a pudendal nerve of the subject, a cavernous nerve of the subject, a spinal nerve root of the subject, a cervical nerve of the subject, a sympathetic nerve of the subject, a parasympathetic nerve of the subject, nervous tissue of the central nervous system of the subject, nervous tissue of the peripheral nervous system of the subject, a nerve of the subject that provides sympathetic innervation to a heart of the subject, a nerve of the subject that provides parasympathetic innervation to a heart of the subject, a nerve of the subject that provides sympathetic innervation to a lung of the subject, a nerve of the subject that provides parasympathetic innervation to a lung of the subject, and a nerve that modulates hidrosis of the subject.

Preferably, driving the current includes selecting at least one parameter of the current in accordance with a stochastic process.

For some applications, the method includes driving the current and suppressing the action potentials at substantially the same time.

In a preferred embodiment, suppressing the action potentials includes regulating the suppressing of the action potentials so as to inhibit an undesired response of the central nervous system of the subject generated responsive to driving the current into the nervous tissue.

In a preferred embodiment, suppressing the action potentials includes regulating the suppressing of the action potentials so as to inhibit an undesired sensation generated responsive to driving the current into the nervous tissue.

Typically, but not necessarily, suppressing the action potentials includes suppressing action potentials induced responsive to driving the current.

As appropriate, driving the current may include configuring the current to be capable of treating one or more of the following: a sleep disorder of the subject, an involuntary movement disorder of the subject, a gastrointestinal motility disorder of the subject, an eating disorder of the subject, obesity of the subject, anorexia of the subject, a gastrointestinal tract disorder of the subject, hypertension of the subject, muscle spasm of the subject, vaginismus of the subject, coma of the subject, an aspect of heart failure of the subject, an aspect of cardiac arrhythmia of the subject, tachycardia of the subject, bradycardia of the subject, or an aspect of chronic obstructive pulmonary disorder (COPD) of the subject.

In a preferred embodiment, the method includes implanting electrodes in a vicinity of the nervous tissue, wherein driving the current includes driving the current through the electrodes on a chronic basis. In another preferred embodiment, the method includes placing electrodes in a vicinity of the nervous tissue in response to an acute occurrence, wherein driving the current includes driving the current through the electrodes, and wherein the method includes removing the electrodes following the acute occurrence.

In a preferred application, driving the current includes configuring the current to be capable of treating epilepsy of the subject. For example, driving the current may include driving the current into a vagus nerve of the subject, and configuring the current to be capable of treating epilepsy of the subject. In this case, suppressing the action potentials may include suppressing action potentials that interfere with an ability of the subject to speak.

In a preferred embodiment, driving the current includes applying to a vagus nerve of the subject a current capable of inducing constriction of a lower esophageal sphincter of the subject.

For some applications, suppressing the action potentials includes suppressing the action potentials repeatedly, during a series of temporally non-contiguous action potential suppression periods. In this case, the method preferably includes substantially withholding the suppressing of action potentials between the action potential suppression periods.

In a preferred embodiment, the method includes sensing an indication of a presence of the condition, wherein driving the current includes driving the current responsive to sensing the indication. For example, the method may include receiving an input from the subject, wherein driving the current includes driving the current responsive to receiving the input.

As appropriate, driving the current may include configuring the current so as to induce action potential propagation primarily in A fibers of the nervous tissue, primarily in B fibers of the nervous tissue, and/or primarily in C fibers of the nervous tissue.

For some applications, driving the current includes configuring the current to be such as to induce action potentials that travel in the first direction in the nervous tissue and collide with and inhibit natural action potentials propagating in the second direction in the nervous tissue. In this case, the step of suppressing action potentials preferably includes suppressing propagation of action potentials that are generated as a result of the step of driving the current into the nervous tissue.

In a preferred embodiment, suppressing the action potentials includes identifying an action potential conduction velocity and suppressing action potentials characterized by the identified conduction velocity. Typically, the method includes withholding suppression of an action potential having a conduction velocity substantially different from the identified conduction velocity.

In a preferred embodiment, suppressing the action potentials includes regulating the suppressing of the action potentials so as to inhibit an undesired effector action responsive to driving the current into the nervous tissue. For example, suppressing the action potentials may include suppressing generation of action potentials that induce increased acid secretion in a gastrointestinal tract of the subject, suppressing generation of action potentials that induce muscular contraction, or suppressing generation of action potentials that induce bradycardia.

For some applications, driving the current includes configuring the current to be capable of treating pain of the subject. In this case (or in the treatment of any of the conditions described herein), driving the current includes applying pulses having pulse durations greater than 0.1 milliseconds. Alternatively or additionally, driving the current includes applying pulses having pulse durations less than 2 milliseconds. Further alternatively or additionally, driving the current includes applying pulses having a frequency less than 50 Hz. For some applications, driving the current includes applying pulses at at least two sites on the nervous tissue, and setting a frequency of pulse application at each site to be less than 30 Hz. Moreover, in accordance with a preferred embodiment of the present invention, driving the current includes applying pulses at at least three sites on the nervous tissue, and setting a frequency of pulse application at each site to be less than 20 Hz. In this case, driving the current may include applying pulses at at least three sites on the nervous tissue, and setting a frequency of pulse application at each site to be less than 10 Hz. For these applications, the method may include designating an inter-site spacing separating each of the at least three sites to be at least 1 centimeter, or at least 3 centimeters.

Preferably, driving the current includes driving a first current between a cathode and a first anode, which are electrically coupled to respective first and second longitudinal sites of the nervous tissue, wherein suppressing the action potentials includes driving a second current through the cathode and a second anode, which second anode is electrically coupled to a third site of the nervous tissue, and wherein the first site is disposed between the second and third sites. In this case, driving the first and second currents includes configuring the second current to be at least 1.5 times greater than the first current. For some applications, driving the first and second currents includes configuring the second current to be at least 3 times greater than the first current.

In accordance with a preferred embodiment of the present invention, driving the current includes driving the current into a nerve of the subject that modulates an aspect of sexual functioning of the subject. For example, driving the current may include configuring the current so as to facilitate engorgement of erectile tissue of the subject. Alternatively or additionally, driving the current includes configuring the current so as to facilitate an orgasmic response by the subject.

For some applications, driving the current includes:

configuring the current in a first mode so as to facilitate engorgement of erectile tissue of the subject; and configuring the current in a second mode, different from the first mode, so as to facilitate an orgasmic response by the subject.

As appropriate, driving the current may include driving the current into a nerve of a male subject or into a nerve of a female subject. Similarly, driving the current may include driving the current into a parasympathetic nerve of the subject or into a sympathetic nerve of the subject, depending on the desired response.

For some applications, driving the current includes configuring the driving of the current such that the first direction includes a direction along the nerve away from a central nervous system (CNS) of the subject.

In this case, driving the current may include:

driving the current into a parasympathetic nerve of the subject; and configuring the current to be such as to induce action potentials that facilitate engorgement of erectile tissue of the subject.

Alternatively or additionally, driving the current may include:

driving the current into a sympathetic nerve of the subject; and configuring the current to be such as to induce action potentials that facilitate an orgasmic response by the subject.

For some applications, driving the current includes configuring the driving of the current such that the first direction includes a direction along the nerve towards a central nervous system (CNS) of the subject.

In this case, driving the current may include:

driving the current into a sympathetic nerve of the subject; and configuring the current to be such as to induce action potentials that travel towards the CNS and collide with and inhibit natural action potentials propagating away from the CNS, which natural action potentials would otherwise inhibit engorgement of erectile tissue of the subject.

Alternatively or additionally, driving the current may include:

driving the current into a parasympathetic nerve of the subject; and configuring the current to be such as to induce action potentials that travel towards the CNS and collide with and inhibit natural action potentials propagating away from the CNS, which natural action potentials would otherwise inhibit an orgasmic response by the subject.

Typically, suppressing the action potentials includes applying an electric field to the nervous tissue. Preferably, applying the field includes applying a plurality of electric fields to the nervous tissue at respective longitudinal sites thereof, e.g., at two adjacent sites separated by at least about 2 mm, or at two adjacent sites separated by less than about 4 mm. Applying the plurality of electric fields to the nervous tissue preferably includes applying each of the fields at a different respective time. For some applications, applying each of the fields at a different respective time includes applying the fields in sequence, in a progression through the respective longitudinal sites of the nervous tissue. For example, applying the fields in sequence may include designating a difference between respective times of application of the fields at two adjacent ones of the sites to be at least 0.1 milliseconds. Moreover, applying the fields in sequence may include designating a difference between respective times of application of the fields at two adjacent ones of the sites to be at least 1 millisecond.

There is further provided, in accordance with a preferred embodiment of the present invention, a method for treating a subject, including:

driving into a sympathetic nerve of the subject a current having a characteristic frequency between about 10 and 50 Hz and an amplitude between about 0.1 and 20 mA; and configuring the driving of the current to be such as to inhibit action potential propagation in the nerve.

There is still further provided, in accordance with a preferred embodiment of the present invention, apparatus for treating a condition of a subject, including:

an electrode device, adapted to be coupled to longitudinal nervous tissue of the subject; and a control unit, adapted to drive the electrode device to apply to the nervous tissue a current which is capable of inducing action potentials that propagate in the nervous tissue in a first direction, so as to treat the condition, and adapted to suppress action potentials from propagating in the nervous tissue in a second direction opposite to the first direction.

In a preferred embodiment, the electrode device includes a tripolar electrode assembly.

Preferably, the tripolar electrode assembly includes a cathode, a first anode, and a second anode. Further preferably, the cathode is disposed between the first and second anodes. Still further preferably, the cathode and the first and second anodes are adapted to be disposed at respective longitudinal sites of the nervous tissue.

There is yet further provided, in accordance with a preferred embodiment of the present invention, apparatus for treating a subject, including:

an electrode device, adapted to apply current to a sympathetic nerve of the subject; and a control unit, adapted to: (a) drive the electrode device to apply to the nerve a current having a characteristic frequency between about 10 and 50 Hz and an amplitude between about 0.1 and 20 mA, and (b) configure the application of the current to be such as to inhibit action potential propagation in the nerve.

The present invention will be more fully understood from the following detailed description of the preferred embodiment thereof, taken together with the drawings, in which:

DETAILED DESCRIPTION OF PREFERRED EMBODIMENTS

Figure 1:
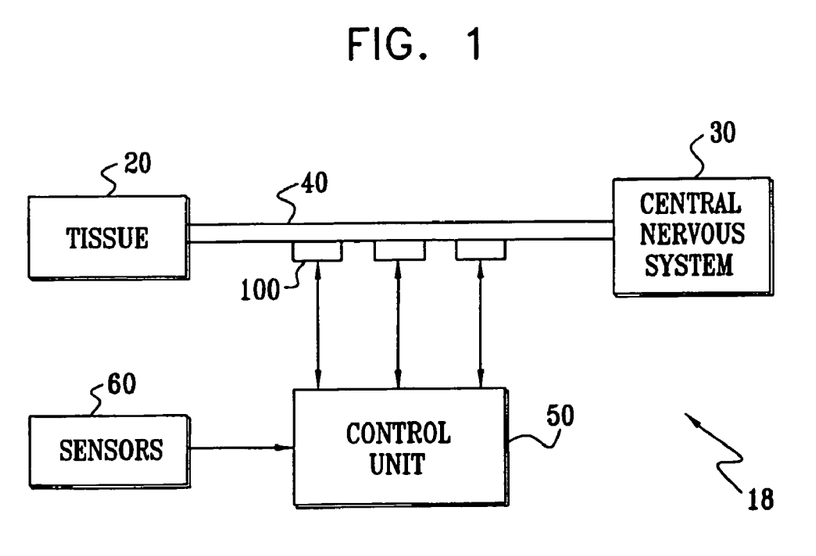
FIG. 1 is a schematic illustration of a nerve, showing the placement of electrode devices thereon, in accordance with a preferred embodiment of the present invention.

FIG. 1 is a schematic illustration of nerve stimulation apparatus 18, for applying electrical energy to induce propagation of impulses in one direction in a nerve 40, in order to treat a condition, while suppressing action potential propagation in the other direction, in accordance with a preferred embodiment of the present invention. For illustrative purposes, nerve 40 may be a cranial nerve, such as the vagus nerve, which emanates from the nervous tissue of the central nervous system (CNS) 30 and transmits sensory signals to CNS 30 and motor or other effector signals to tissue 20. Apparatus 18 typically comprises an implantable or external control unit 50, which drives one or more electrode devices 100 to apply an appropriate signal to respective sites on nerve 40. It is to be understood that whereas preferred embodiments of the present invention are described herein with respect to controlling propagation in a nerve, the scope of the present invention includes applying signals to other nervous tissue, such as individual axons or nerve tracts.

Preferably, control unit 50 receives and analyzes signals from sensors 60 located at selected sites in, on, or near the body of the patient. These sensor signals are typically qualitative and/or quantitative measurements of a medical, psychiatric and/or neurological characteristic of a disorder being treated. For example, sensors 60 may comprise electroencephalographic (EEG) apparatus to detect the onset of a seizure, or a user input unit, adapted to receive an indication of a level of discomfort, hunger, or fatigue experienced by the patient. Preferably, the sensor signals are analyzed within control unit 50, which, responsive to the analysis, drives electrode devices 100 to apply current to one or more sites on nerve 40, configured such that application thereof stimulates unidirectional propagation of nerve impulses to treat the specific disorder of the patient.

Alternatively, nerve stimulation apparatus 18 operates without sensors 60. In such a preferred embodiment, control unit 50 is typically preprogrammed to operate continuously, in accordance with a schedule, or under regulation by an external source.

For some applications of the present invention, the signals applied by control unit 50 to electrode devices 100 are configured to induce efferent nerve impulses (i.e., action potentials propagating in the direction of tissue 20), while suppressing nerve impulses traveling in nerve 40 towards CNS 30. For illustrative purposes, tissue 20 may comprise muscle tissue of the gastrointestinal tract, and treatment of motility disorders may be accomplished by inducing propagation of nerve impulses towards the muscle tissue, while suppressing the propagation of nerve impulses to CNS 30. Preferably, methods and apparatus described in U.S. Pat. No. 5,540,730 to Terry et al. are adapted for use with this embodiment of the present invention. In contrast to the outcome of application of the apparatus described in the Terry patent, however, in this embodiment of the present invention, CNS 30 substantially does not receive sensory signals that could potentially generate undesired responses.

Alternatively or additionally, gastroesophageal reflux disease (GERD) is treated by stimulating the vagus nerve unidirectionally, in order to induce constriction of the lower esophageal sphincter. Advantageously, such an application of unidirectional stimulation inhibits or substantially eliminates undesired sensations or other feedback to the central nervous system which would in some cases be induced responsive to stimulation of the vagus nerve. It is noted that this suppression of afferent impulses is typically only applied during the relatively short time periods during which pulses are applied to the vagus nerve, such that normal, physiological afferent impulses are in general able to travel, uninhibited, towards the CNS. For some applications, apparatus and methods described in the above-cited U.S. Pat. Nos. 5,188,104, 5,716,385 or 5,423,872 are adapted for use with unidirectional stimulation as provided by this embodiment of the present invention.

For some applications of the present invention, electrode devices 100 are configured to induce afferent impulses (i.e., action potentials propagating in the direction of CNS 30), while suppressing impulses in the direction of tissue 20. Typically, conditions such as eating disorders, coma, epilepsy, motor disorders, sleep disorders, hypertension, and neuropsychiatric disorders are treated by adapting techniques described in one or more of the above-cited references for use with therapeutic unidirectional impulse generation as provided by these embodiments of the present invention. Advantageously, this avoids unwanted and not necessarily beneficial outcomes of the prior art technique, such as bradycardia, enhanced gastric acid secretion, or other effects secondary to stimulation of the vagus nerve and communication of unintended nerve impulses to tissue 20. Which specific tissue 20 receives the efferent stimulation unintentionally induced by the prior art techniques depends upon the location on the nerve at which the stimulation is applied. For example, branchial motor efferents of the vagus nerve supply the voluntary muscles of the pharynx and most of the larynx, as well as one muscle of the tongue. The visceral efferents include parasympathetic innervation of the smooth muscle and glands of the pharynx, larynx, and viscera of the thorax and abdomen. Consequently, unintended efferent signal generation may induce undesired or unexpected responses in any of the tissue controlled and regulated by the vagus nerve. In preferred embodiments of the present invention, by contrast, such responses are suppressed while, at the same time, the desired afferent nerve signals are transmitted to CNS 30.

A variety of methods for inducing unidirectional propagation of action potentials are known in the art, some of which are described in the references cited in the Background section of the present patent application and may be adapted for use with preferred embodiments of the present invention.

In a preferred embodiment, unidirectional signal propagation is induced using methods and apparatus disclosed in:

U.S. Provisional Patent Application 60/263,834 to Cohen and Ayal, filed Jan. 25, 2001, entitled "Selective blocking of nerve fibers," which is assigned to the assignee of the present patent application and is incorporated herein by reference, U.S. patent application Ser. No. 09/824,682, filed Apr. 4, 2001, entitled "Method and apparatus for selective control of nerve fibers," to Cohen and Ayal, which is assigned to the assignee of the present patent application and is incorporated herein by reference, A PCT application, filed on even date with the present patent application, entitled "Method and apparatus for selective control of nerve fibers," to Cohen and Ayal, which is assigned to the assignee of the present patent application and is incorporated herein by reference, and/or the above-cited U.S. Pat. Nos. 5,199,430, 4,628,942, and/or 4,649,936.

The Cohen and Ayal regular patent application describes a method for:

(a) selectively suppressing the propagation of naturally-generated action potentials which propagate in a predetermined direction at a first conduction velocity through a first group of nerve fibers in a nerve bundle, while (b) avoiding unduly suppressing the propagation of naturally-generated action potentials propagated in the predetermined direction at a different conduction velocity through a second group of nerve fibers in the nerve bundle.

The method includes applying a plurality of electrode devices to the nerve bundle, spaced at intervals along the bundle. Each electrode device is capable of inducing, when actuated, unidirectional "electrode-generated" action potentials, which produce collision blocks with respect to the naturally-generated action potentials propagated through the second group of nerve fibers. Moreover, each electrode device is actuated in sequence, with inter-device delays timed to generally match the first conduction velocity and to thereby produce a wave of anodal blocks, which: (a) minimize undesired blocking of the naturally-generated action potentials propagated through the first group of nerve fibers, while (b) maximizing the generation rate of the unidirectional electrode-generated action potentials which produce collision blocks of the naturally-generated action potentials propagated through the second group of nerve fibers. Such a method may be used for producing collision blocks in sensory nerve fibers in order to suppress pain, and also in motor nerve fibers to suppress selected muscular or glandular activities.

Alternatively or additionally, embodiments of the present invention induce the propagation of unidirectional action potentials using techniques described in the above-cited U.S. Pat. Nos. 4,649,936 to Ungar et al., and 4,608,985 to Chrish et al., which describe apparatus and methods for selectively blocking action potentials passing along a nerve trunk. In this case, electrode device 100 comprises an asymmetric, single electrode cuff, which includes an electrically non-conductive or dielectric sleeve that defines an axial passage therethrough. The dielectric sheath and axial passage extend from a first end, which is disposed toward the origin of orthodromic pulses, to a second end. The gap between the nerve and the cuff is filled by conductive body tissues and fluids after implantation in the body. A single annular electrode is disposed in the axial passage, which may be mounted on the inner surface of the dielectric sleeve within the axial passage. Other implementation details may be found in the Ungar and Chrish patents.

It is to be understood that whereas preferred embodiments of the present invention are generally described hereinabove with respect to stimulating and inhibiting action potential propagation in the vagus nerve, the scope of the present invention includes applying analogous techniques to other central or peripheral nervous tissue of a patient.

Figure 2:
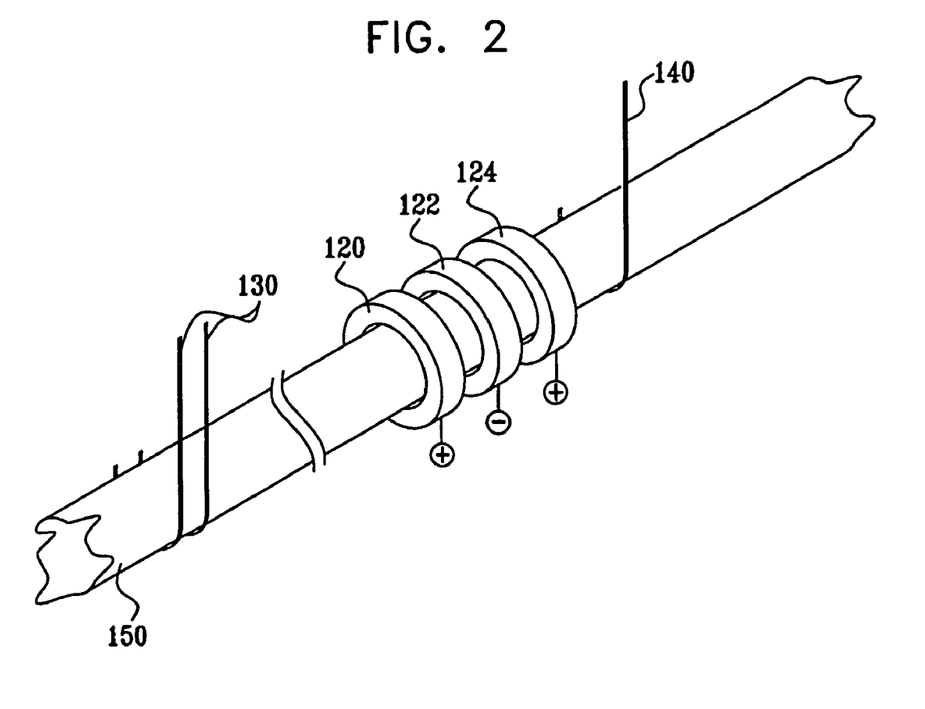
FIG. 2 is a schematic illustration of a nerve and experimental apparatus applied thereto, in accordance with a preferred embodiment of the present invention.
Figure 3A:
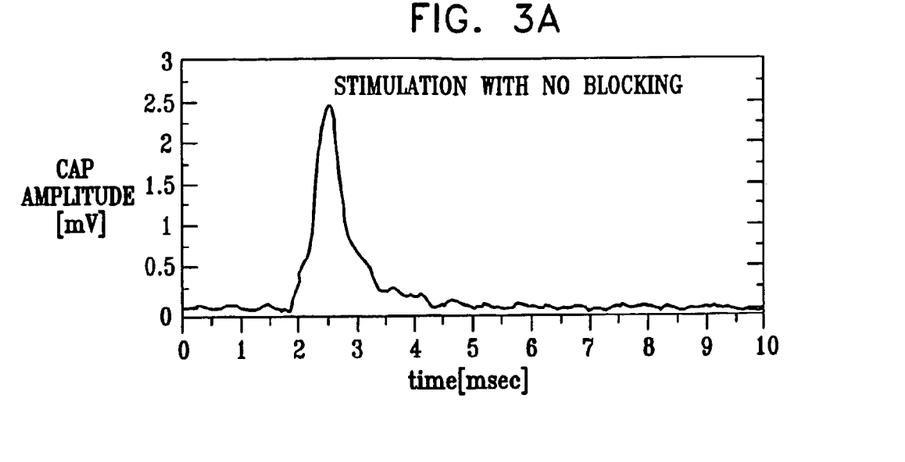
FIGS. 3A, 3B, and 3C are graphs showing data measured using the experimental apparatus of FIG. 2.
Figure 3B:
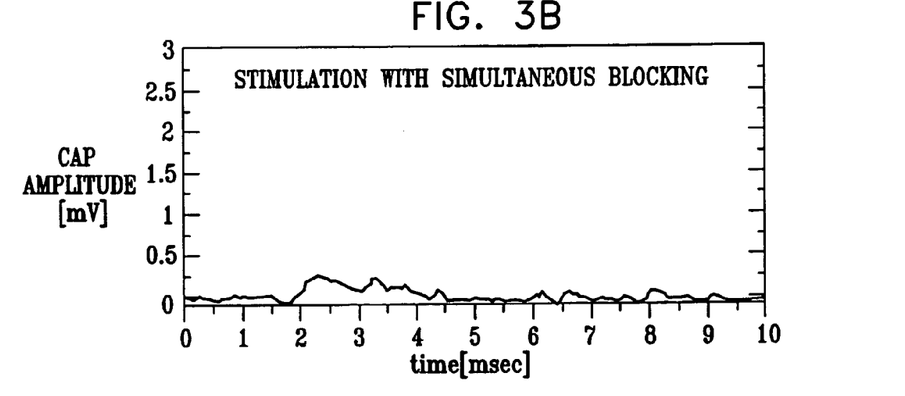
Figure 3C:
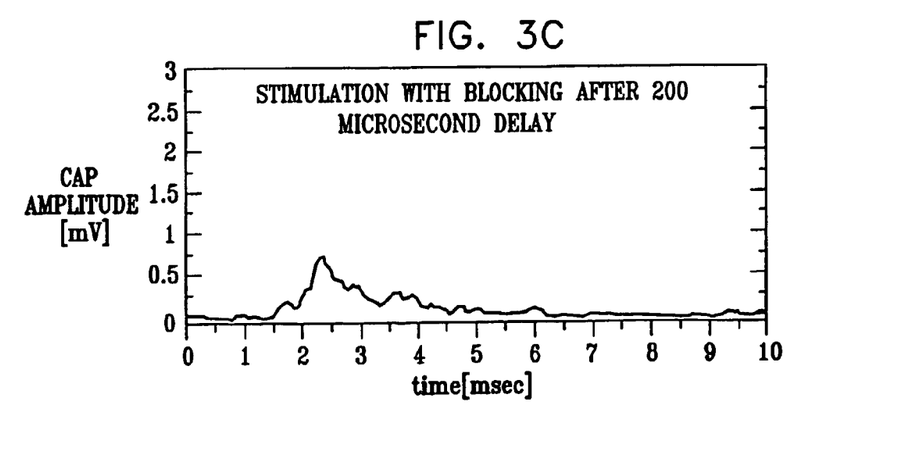

Reference is now made to FIGS. 2, 3A, 3B, and 3C. FIG. 2 is a schematic illustration of experimental apparatus which was applied to a rat sciatic nerve 150, in order to block the propagation of action potentials in A fibers thereof, in accordance with a preferred embodiment of the present invention. FIGS. 3A, 3B, and 3C are graphs showing experimental results attained during the use of the apparatus of FIG. 2, in accordance with a preferred embodiment of the present invention.

Bipolar hook electrodes 130 coupled to a stimulus isolator were placed in contact with nerve 150, and were driven to apply a 20 microsecond, 2 mA square pulse to the nerve. In this experimental preparation, these parameters were found to yield maximal compound action potentials (CAPs), as measured at a recording site by another hook electrode 140.

A tripolar platinum/iridium (Pt/Ir) cuff electrode assembly comprising individual electrodes 120, 122, and 124 was applied to nerve 150 between electrodes 130 and 140. The electrodes in the cuff were separated by gaps of 1 mm from each other, and the overall length of the cuff was 5 mm. (The cuff structure holding electrodes 120, 122, and 124 in place is not shown.) Current was applied to the electrode assembly through two stimulus isolators coupled to a D/A computer card, and was configured such that electrode 122 served as a cathode, and electrodes 120 and 124 served as anodes. A unidirectional action potential was generated by driving through electrode 122 a total cathodic current of 0.8 mA, and controlling electrodes 120 and 124 such that 0.1 mA passed through electrode 120, and 0.7 mA passed through electrode 124. The 0.1 mA was found to be sufficient to generate an action potential traveling towards electrodes 130, which collided with and ended propagation of action potentials generated by hook electrodes 130. Similarly, the 0.7 mA was found to be sufficient to inhibit propagation of action potentials which were generated responsive to the operation of the cuff electrode assembly. In these experiments, the current driven through electrodes 120, 122, and 124 was quasi-trapezoidal in time, having a duration of 200 microseconds and a decay constant of 300 microseconds.

FIG. 3A shows the results of application of a stimulation pulse through electrodes 130, without any blocking applied through the electrode assembly of electrodes 120, 122, and 124. A complete compound action potential, characteristic of this preparation, is seen to peak at approximately T=2.5 milliseconds. In FIG. 3B, stimulation was applied through electrodes 130 at the same time that electrodes 120, 122, and 124 drove blocking currents into nerve 150 as described hereinabove. The CAP is seen to be very significantly reduced, because the action potentials traveling in one direction from electrodes 130 collided with the "blocking" action potentials propagating in the other direction from electrodes 120 and 122. In FIG. 3C, the stimulation through electrodes 130 was followed, after a 200 microsecond delay, by the generation of the blocking currents through electrodes 120, 122, and 124. In this case, it is seen that action potentials propagating through faster fibers had already passed the cuff electrode assembly by the time that the action potentials propagating from electrode 120 had been initiated. Since there was no elimination by collision, the fastest moving action potentials leaving electrodes 130 were detected by electrode 140. However, slower action potentials were eliminated, such that the overall CAP area is seen to be significantly smaller in FIG. 3C than in FIG. 3A.

For some applications, this technique is utilized to affect action potential propagation in the pelvic nerve, or in another nerve, in order to treat erectile dysfunction. Preferably, the signals applied are configured so as to cause the arterial dilation responsible for erection, e.g., by collision-blocking action potentials propagating in sympathetic C fibers which innervate arteries of the penis that, when constricted, prevent erection. By inhibiting action potential propagation in these fibers, the arteries dilate, and erection is achieved. Preferably, the signal is applied in a unidirectional mode, so as to prevent undesired action potentials from being conveyed to the penis in response to the applied signal.

Alternatively or additionally, high frequency blocking currents are applied to sympathetic fibers, e.g., at frequencies above approximately 500 Hz, so as to reduce arterial constriction and facilitate erection. Further alternatively or additionally, simple anodal block is applied to the sympathetic fibers, using techniques known in the art or described herein, in order to facilitate erection.

In combination with some of these techniques, or separately therefrom, stimulation may be applied to parasympathetic fibers, in order to facilitate erection. Preferably, the stimulation is applied at a pelvic site in a unidirectional mode, such that unpleasant or painful signals are not conveyed to the brain in response to the applied stimulation. Typically, stimulation currents having frequencies in the range of 10-50 Hz are applied to the pelvic or pudendal nerves.

In a preferred embodiment, collision blocking or another inhibitory electrical signal is applied to parasympathetic fibers in order to support ejaculation preferably following a period of erection. Alternatively or additionally, ejaculation is facilitated by electrical stimulation applied to sympathetic fibers.

For some applications, nerve stimulation or inhibition techniques described herein are used in the treatment of heart failure or in the treatment of other cardiac pathologies, e.g., arrhythmias such as fibrillation, tachycardia, or bradycardia. By way of analogy to beta blockers, which are known to inhibit sympathetic input to the heart and thereby treat tachycardia and heart failure, some embodiments of the present invention electrically inhibit the heart's sympathetic input in order to reduce cardiac contractility and rate. By contrast to beta blockers, however, these embodiments of the present invention do not have the disadvantages associated with pharmaceutical regimes (e.g., a need to follow a daily pill-taking schedule, as well as possible systemic effects of the beta blockers). As a result of these and other disadvantages, beta blockers are not suitable for a significant portion of the patient population.

Typically, electrical inhibition as provided by these preferred embodiments of the present invention is applied to sympathetic fibers by means of one or more of the following techniques described herein: (a) anodal blocking, (b) high-frequency blocking, preferably applied in a unidirectional mode, or (c) inhibiting action potentials which are coming from the CNS to the heart, by sending collision-blocking action potentials from an electrode implantation site on a nerve, along C fibers thereof, towards the CNS. This latter technique is also preferably applied in a unidirectional mode, so as to minimize action potential propagation towards the heart responsive to the applied signals. These techniques may be practiced using electrodes implanted on or placed in the vicinity of any one or more sympathetic nerves innervating the heart, such as, for example, thoracic branches of the superior cervical nerve, the middle cervical nerve, or the inferior cervical nerve.

Alternatively or additionally, parasympathetic stimulation of the heart is enhanced, in order to achieve a result generally similar to that of beta blockers. For example, electrodes may be placed on the portion of the vagus nerve that innervates the heart, and driven in a unidirectional mode to enhance the parasympathetic signaling regulating the heart, substantially without causing undesired action potentials to propagate towards the CNS responsive to the applied stimuli.

Preferably, sympathetic inhibition and/or parasympathetic stimulation as described are applied in response to one or more sensed cardiac parameters or other physiological parameters, such as heart rate, electrocardiogram, blood pressure, or indicators of decreased cardiac contractility. Alternatively, the stimulation or inhibition is applied intermittently, constantly, based on the time of day, or in response to a patient input.

For some applications, chronic obstructive pulmonary disease (COPD) is treated by inhibiting parasympathetic stimulation of the lungs, using any of the techniques described herein, e.g., (a) anodal blocking of parasympathetic fibers innervating the lungs, (b) high-frequency blocking of parasympathetic fibers innervating the lungs, preferably applied in a unidirectional mode, and/or (c) inhibition of parasympathetic action potentials coming from the CNS to the lungs, by sending collision-blocking action potentials from an electrode implantation site on a nerve, preferably along C fibers thereof, towards the CNS. Preferably, this latter technique is practiced in a unidirectional mode, so as to avoid sending additional action potentials towards the lungs as a result of the applied currents. In addition to or in place of these techniques, sympathetic nerves innervating the lung may be stimulated, so as to enhance the sympathetic pulmonary response and treat the COPD. These techniques, applied separately or in combination, are believed to be well-suited for many patient populations, e.g., asthmatics, and are preferably configured so as to avoid, replace, or reduce the pharmaceutical regimes which many COPD patients must follow, such as frequent inhaler use.

In other applications, hyperhidrosis (excess sweating) is treated by suppressing action potentials from propagating in sympathetic fibers innervating sweat glands. For example, any of the inhibition techniques described herein may be adapted for use with electrodes placed on a nerve leaving one of the cervicothoracic ganglia towards one of the patient's arms, in order to facilitate a reduction of perspiration by the axillary sweat glands. In particular, preferred techniques include: (a) anodal blocking of sympathetic fibers innervating the axillary sweat glands, (b) high-frequency blocking of sympathetic fibers innervating the axillary sweat glands, preferably applied in a unidirectional mode, and/or (c) inhibition of sympathetic action potentials coming from the cervicothoracic ganglion to the axillary sweat glands, by sending collision-blocking action potentials from an electrode implantation site on a suitable nerve towards the cervicothoracic ganglia.

In a preferred embodiment, pain is treated by applying a tripolar electrode array at a peripheral nerve site between a source of chronic pain and the central nervous system (CNS). Preferably, unidirectional collision blocking is applied, as described above, so as to eliminate centrally-propagating pain signals, while substantially not generating centrally-propagating action potentials in response to the application of current by the tripolar electrode array. Preferably, the collision blocking is configured so as to block pain signals but not other sensory signals.

Advantageously, pain signals generally travel through very small fibers, while other sensory information often propagates in larger fibers. As such, the tripolar electrode array (e.g., as shown in FIG. 2) is preferably driven for between 0.1 and 2 milliseconds, typically 0.3 milliseconds, and a greater amount of current is driven through the electrode proximal to the CNS, and less current through the electrode distal to the CNS. Preferably, the ratio of these two currents is between about 3:1 and 15:1. The inventors of the present patent application have found that a stimulation protocol such as this generally generates peripherally-directed action potentials in the pain-carrying fibers, which ultimately collide with and destroy centrally-directed pain signals traveling through the same fibers. Further, this protocol minimizes the generation of peripherally-directed action potentials in the larger fibers, and thus avoids collision-blocking of non-pain sensory signals traveling through these fibers.

If the creation rate of collision-blocking action potentials in the pain fibers is sufficiently high, e.g., O(40 Hz), then a substantial portion of the pain signals traveling through the nerve will be destroyed. It is specifically noted that no sensing of upstream pain signals is necessary, nor is a patient input required. It is also noted that although pain fibers carrying a pain signal often transmit approximately 40 action potentials each second, it may be desirable in some instances to intentionally allow some of the pain signals to pass, in order to guarantee that the patient remains aware of potentially dangerous conditions in her environment.

A side effect of the pain-treatment technique described hereinabove is that action potentials propagating in non-pain fibers in either direction may be destroyed if the non-pain action potentials are under the tripolar electrode assembly during the short period in which unidirectional action potentials are being created. An adverse result of aggressive pain treatment (e.g., at 40 Hz), therefore, might theoretically include partial numbness or weakness. The inventors have determined, however, that the use of multiple tripolar electrode arrays, disposed at respective longitudinal sites along a nerve, can substantially reduce this potentially adverse effect to the point where it does not interfere with the patient's activities of daily living and/or is not even noticed by the patient.

Preferably, the tripolar electrodes at the different sites are driven to generate unidirectional action potentials in a manner analogous to a wave of green traffic lights, whereby if an action potential traveling through a non-pain fiber is not eliminated at one of the tripolar electrodes, then it is unlikely to be eliminated at any other tripolar electrode. In particular, this method can be optimized to allow action potentials having a predetermined range of conduction velocities to pass through the plurality of tripolar electrodes.

For example, if it is desired to allow most 50 m/s action potentials to pass through, unimpeded by the generation of unidirectional action potentials, and if a plurality of tripolar electrode arrays are spaced one every 5 centimeters along a nerve, then each tripolar electrode array is preferably activated 1 millisecond after its neighbor. If, in this example, five such tripolar electrode arrays are implanted and activated in a wave, and if it is desired to eliminate pain-conveying action potentials 40 times each second, then each individual tripolar electrode array is only activated 8 times per second. Consequently, the relatively high frequency non-pain action potentials are only blocked approximately 8 times per second, which is so low compared to the number of non-pain action potentials which are allowed to pass, that this is not expected to have any significant clinical repercussions. Conversely, the undesired pain signals are minimized by this treatment.

Preferably, a calibration procedure is invoked in order to set both the timing of the generation of the wave, and the relative currents applied to the anodes in each tripolar electrode. Advantageously, the plurality of tripolar electrodes at their respective sites along the nerve can be used in and of themselves to facilitate the calibration, without the need for other electrical sensors to be applied to the nerve. That is, the timing and current profiles of one of the tripolar electrodes can be varied while its effect is recorded by the other tripolar electrodes at their respective sites.

It has been observed that the human body can lose sensitivity to a constant stimulation protocol. The above-cited U.S. Pat. No. 4,338,945 to Kosugi et al. notes, for example, that randomizing an applied electrical stimulation enhances pain relief. Preferred embodiments of the present invention utilize methods described in the Kosugi patent, mutatis mutandis, or other stochastic methods, as appropriate, in order to randomize one or more parameters of the signals applied to nerves, and thereby enhance the efficacy of the treatments. By thus avoiding using a predetermined signal, the body's desired response can typically be elicited for a longer time period.

For some applications, techniques described herein are carried out using methods and apparatus described in U.S. patent application Ser. No. 09/843,334, filed Apr. 26, 2001, entitled, "Actuation and control of limbs through motor nerve stimulation," which is assigned to the assignee of the present patent application and incorporated herein by reference.

It is noted that while some preferred embodiments of the present invention utilize a permanently-implanted set of electrodes, configured to apply currents as described for many years, the scope of the present invention includes the use of these techniques in an acute setting, e.g., after cardiac arrest, in order to treat a condition.

It is to be understood that many of the inhibitory techniques described herein for application to sympathetic or parasympathetic fibers may be applied in combination with—or may be replaced by—stimulation of parasympathetic or sympathetic fibers, respectively.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. For example, specific electrical treatments are described herein for specific clinical conditions by way of example, but those of ordinary skill in the art will understand that the same treatments may be applied to the same or other nerves in the treatments of other conditions. In particular, unless there is a specific clinical counter-indication or other counter-indication, it is to be understood that the scope of the present invention includes applying any of the sensing and signal application modes described herein and/or recited explicitly in the various claims, either: (a) in the treatment of each medical condition cited herein and/or recited explicitly in the various claims, or (b) in the treatment of the symptoms or causes of other medical conditions.

The invention claimed is:

1. A method for treating a condition of a subject, comprising:
    driving into longitudinal nervous tissue of the subject a stimulating current at a first longitudinal location which is capable of inducing action potentials that propagate in the nervous tissue in a first direction which action potentials include slower and faster action potentials; and
    suppressing the slower action potentials from propagating in the nervous tissue in the first direction by applying a blocking current at a second longitudinal location after a delay following driving the stimulating current, and timing the delay to allow passage of the faster action potentials, while suppressing the slower action potentials,
    wherein the longitudinal nervous tissue includes at least one nerve selected from the group consisting of: a sympathetic nerve of the subject, and a parasympathetic nerve of the subject.

2. A method according to claim 1, wherein driving the stimulating and blocking currents comprises driving the stimulating and blocking currents into tissue selected from the group consisting of: a pudendal nerve of the subject, a cavernous nerve of the subject, a spinal nerve root of the subject, and a cervical nerve of the subject.

3. A method according to claim 1, wherein driving the stimulating and blocking currents comprises driving stimulating and blocking currents into the parasympathetic nerve of the subject.

4. A method according to claim 3, wherein driving the stimulating and blocking currents comprises driving the stimulating and blocking currents into a nerve of the subject that provides parasympathetic innervation to a heart of the subject.

5. A method according to claim 1, wherein driving the stimulating and blocking currents comprises driving the stimulating and blocking currents into at least one nerve of the subject selected from the group consisting of:
    (a) a nerve of the subject that provides sympathetic innervation to a lung of the subject, and
    (b) a nerve of the subject that provides parasympathetic innervation to a lung of the subject, and
    (c) a nerve that modulates hidrosis of the subject.

6. A method according to claim 1, wherein driving the stimulating and blocking currents comprises at least one of the group consisting of:
    (a) configuring the currents to be capable of treating muscle spasm of the subject, and
    (b) configuring the currents to be capable of treating vaginismus of the subject.

7. A method according to claim 1, wherein driving the stimulating and blocking currents comprises configuring the stimulating and blocking currents to be capable of treating an aspect of heart failure of the subject.

8. A method according to claim 1, wherein driving the stimulating and blocking currents comprises configuring the stimulating and blocking currents to be capable of treating an aspect of cardiac arrhythmia of the subject.

9. A method according to claim 1, wherein driving the stimulating and blocking currents comprises configuring the stimulating and blocking currents to be capable of treating tachycardia of the subject.

10. A method according to claim 1, wherein driving the stimulating and blocking currents comprises configuring the stimulating and blocking currents to be capable of treating bradycardia of the subject.

11. A method according to claim 1, wherein driving the stimulating and blocking currents comprises configuring the stimulating and blocking currents to be capable of treating an aspect of chronic obstructive pulmonary disorder (COPD) of the subject.

12. A method according to claim 1, and comprising implanting electrodes in a vicinity of the nervous tissue, wherein driving the stimulating and blocking currents comprises driving the stimulating and blocking currents through the electrodes on a chronic basis.

13. A method according to claim 1, and comprising placing electrodes in a vicinity of the nervous tissue in response to an acute occurrence, wherein driving the stimulating and blocking currents comprises driving the stimulating and blocking currents through the electrodes, and wherein the method comprises removing the electrodes following the acute occurrence.

14. A method according to claim 1, wherein driving the stimulating and blocking currents comprises configuring the stimulating and blocking currents so as to induce action potential propagation primarily in A fibers of the nervous tissue.

15. A method according to claim 1, wherein driving the stimulating and blocking currents comprises driving the stimulating and blocking currents into the sympathetic nerve of the subject.

16. A method according to claim 15, wherein driving the stimulating and blocking currents comprises driving the stimulating and blocking currents into a nerve of the subject that provides sympathetic innervation to a heart of the subject.

17. A method according to claim 1, wherein suppressing the slower action potentials comprises configuring the blocking current to eliminate, by collision blocking, the slower action potentials propagating in the second direction.

18. A method according to claim 1, wherein the delay has a duration of 200 microseconds.

* * * * *